United States Patent
Mathews et al.

(10) Patent No.: US 7,244,814 B2
(45) Date of Patent: Jul. 17, 2007

(54) VARIANT TAT PROTEINS AND METHODS FOR USE THEREOF

(75) Inventors: Michael B. Mathews, Monclair, NJ (US); Tsafi Pe'ery, Monclair, NJ (US); Syed Reza, Cross Lanes, WV (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 71 days.

(21) Appl. No.: 10/505,265

(22) PCT Filed: Feb. 21, 2003

(86) PCT No.: PCT/US03/05041

§ 371 (c)(1),
(2), (4) Date: Apr. 22, 2005

(87) PCT Pub. No.: WO03/072709

PCT Pub. Date: Sep. 4, 2003

(65) Prior Publication Data

US 2005/0221288 A1   Oct. 6, 2005

Related U.S. Application Data

(60) Provisional application No. 60/358,595, filed on Feb. 21, 2002.

(51) Int. Cl.
*C07K 5/00* (2006.01)
*A61K 39/21* (2006.01)

(52) U.S. Cl. .................... 530/300; 424/208.1
(58) Field of Classification Search ................ 530/300; 424/208.1
See application file for complete search history.

(56) References Cited

OTHER PUBLICATIONS

Roof, P. et al., Differential regulation of HIV-1 clade-specific B, C, and E long terminal repeats by NF-kB and the Tat transactivator, Virology (2002), 296:77-83.*
Reza et al., "A Naturally Occurring Substitution in Human Immunodeficiency Virus Tat Increases Expression of the Viral Genome", Journal of Virology 2003 77 (15) :8602-8606.
NCBI Database Accession No. P05908 [gi:135350] Jun. 15, 2002.

* cited by examiner

*Primary Examiner*—Bruce R. Campell
*Assistant Examiner*—Nicole Kinsey
(74) *Attorney, Agent, or Firm*—Licata & Tyrrell P.C.

(57) ABSTRACT

Variants of the HIV-1 Tat protein exhibiting higher transcriptional activation and stronger P-TEFb binding than wild-type Tat are provided. In addition variants that can inhibit transcription activation by wild-type Tat are provided. Nucleic acid sequences encoding these variants, vectors and host cells for expression of these variants, and antibodies raised against these variants are also provided. In addition, methods for use of these variants and compositions containing these variants as research tools, as diagnostic tools and in the treatment of viral infections are provided.

6 Claims, No Drawings

VARIANT TAT PROTEINS AND METHODS FOR USE THEREOF

This application is a 35 U.S.C. 371 filing of PCT/US03/05041, filed Feb. 21, 2003, which claims priority to U.S. Provisional patent application Ser. No. 60/358,595, filed Feb. 21, 2002.

This invention was supported in part by funds from the U.S. government (NIH Grant Nos. AI31802 and AI34552) and the U.S. government may therefore have certain rights in the invention.

FIELD OF THE INVENTION

This present invention relates to new variants of the Tat protein that exhibit higher transcriptional activation than wild-type Tat. The new variants, referred to herein as "Super-Tats", also bind P-TEFb more strongly than wild-type Tat. Super-Tats of the present invention are useful as research tools in studying viral replication, as diagnostic tools for determination of viral infection, and in the treatment of viral infections.

BACKGROUND OF THE INVENTION

The human immunodeficiency virus type 1 (HIV-1) Tat protein is a key regulatory protein in the HIV-1 replication cycle. Wild-type Tat gene of HIV-1 is required for production of viral RNA and viral replication. Tat interacts with cellular transcriptional factors and cytokines, such as tumor necrosis factor-alpha (TNF-alpha), and alters the expression of a variety of genes in HIV-1-infected and non-infected cells. Tat function requires its binding to a cellular positive transcription elongation factor b (P-TEFb).

The presence of Tat specific cytotoxic T lymphocytes is correlated with strong resistance to HIV infection (Allen et al. Nature 2000 407(6802):386–390). Tat mediated pathogenic effects can also be neutralized by anti-Tat antibodies. Antibodies directed against conserved regions of Tat, such as the cysteine rich and the lysine rich domains, have been shown to be particularly effective in inhibiting HIV replication. In HIV-1-infected patients, a strong humoral immune response against HIV-1 Tat protein is inversely correlated to peripheral blood viral load (Re et al. J. Clin. Virol. 2001 21(1):81–9)

Wild-type Tat also promotes lymphocyte infiltration and adhesion primarily by its binding to VEGF receptor and its subsequent dimerization and activation (Mitola et al. Blood 1997 90(4):1365–72). This effort is primarily mediated by the basic domain of Tat.

Wild-type Tat modified to be defective in binding to TAR has been shown to be effective in inhibiting viral long terminal repeat (LTR) transactivation (Modesti et al. New Biol. 1991 3(8):759–68).

Tat has also been shown to be taken up and internalized by cells. Thus, fusion of a heterologous protein to Tat has been proposed as a means for cellular delivery of heterologous proteins in cell culture and living animals.

However, Tat has also been linked with multiple pathogenic effects. For example, numerous studies indicate a role for the HIV regulatory protein Tat in HIV-related inflammatory and neurodegenerative processes. HIV-1 Tat protein has been linked to dementia associated with HIV infection. In addition, the Tat protein has been directly implicated in the pathogenesis of AIDS-related Kaposi's sarcoma. More recently, with the advent of agents which prolong the life of HIV-infected patients, secretion of the Tat protein has been implicated in multiple cardiovascular diseases observed in these patients (Krishnaswamy et al. Cardiology in Review 2000 8(5):260–8). Thus, while Tat administration has multiple utilities, it also causes multiple pathogenic effects.

In the present invention, variants of Tat, referred to herein as Super-Tats, are provided which exhibit similar but enhanced activities as compared to wild-type Tat. Accordingly Super-Tats of the present invention can be administered at lower levels in clinical application thereby minimizing pathogenic effects associated with Tat administration.

SUMMARY OF THE INVENTION

An object of the present invention is to provide variants of the wild-type HIV-1 Tat protein, also referred to herein as Super-Tats, which exhibit higher transcriptional activation and stronger P-TEFb binding than wild-type HIV-1 Tat.

Another object of the present invention is to provide nucleic acid sequences encoding Super-Tats, vectors comprising these nucleic acid sequences and host cells comprising these vectors which are capable of encoding Super-Tats.

Another object of the present invention is to provide methods for production of Super-Tats. In one embodiment, Super-Tats of the present invention can be prepared via chemical synthesis. In another embodiment, Super-Tats can be prepared recombinantly.

Another object of the present invention is to provide methods of using Super-Tats in place of wild-type HIV-1 Tat in research applications, as an endothelial permeability factor, to inhibit viral transcription and to selectively activate latently infected cells.

Another object of the present invention is to provide antibodies raised against a Super-Tat, antiviral vaccines comprising anti-Super-Tat antibodies and methods of using these vaccines to protect against HIV infection and to neutralize the pathogenic effects of the Tat protein.

Another object of the present invention is to provide compositions comprising a Super-Tat.

In one embodiment, the composition is a fusion protein comprising a Super-Tat fused to another selected protein such as an enzyme. In this embodiment, the Super-Tat facilitates uptake into cells of the selected protein fused thereto.

In another embodiment, the composition is a tagged fusion construct comprising a Super-Tat fused to a tag useful in purifying the Super-Tat. Examples of such tags include, but are not limited to, HIS and FLAG.

In another embodiment, the composition is an HIV-1 molecular clone, an HIV virus or a virus such as a SHIV (simian/human chimera virus) comprising a Super-Tat. These compositions are useful for studying the effect of highly active Tat on viral replication and latency.

In another embodiment, the composition is conditioned medium from cells expressing Super-Tat. Conditioned medium from cells expressing Super-Tat has a variety of uses including, but not limited to, purification of Super-Tat, growth medium for viral replication, and in diagnostic assays.

Accordingly, yet another object of the present invention is to provide methods and kits for diagnosing HIV infection in an individual via a conditioned medium from cells expressing Super-Tat.

DETAILED DESCRIPTION OF THE INVENTION

The present invention relates to variants of the HIV-1 Tat protein, referred to herein as “Super-Tats”, that exhibit higher transcriptional activation and stronger P-TEFb binding than wild-type HIV-1 Tat. It has now been found that the introduction of a T23N change (threonine to asparagine at position 23) in wild-type HIV-1 (strain NL4-3) Tat, results in a more active protein. In particular, this Super-Tat exhibited 5-fold higher transcription activation and 3.5-fold stronger P-TEFb binding than wild-type Tat of the NL4-3 strain. Other amino acid residues examined at this position such as Q, D, E, H, V, A, I, P, S had either deleterious or no effect on the activity of Tat. Still other amino acid substitutions at this residue are expected to result in highly active forms of Tat.

The present invention also relates to methods for production of Super-Tats. Various methods for production of the Super-Tats of the present invention can be used.

In one embodiment, the Super-Tats of the present invention can be chemically synthesized in accordance with well known techniques for peptide synthesis.

In another embodiment, Super-Tats of the present invention can be prepared recombinantly in a host cell transfected with a vector capable of encoding the Super-Tat in the host cells. Various vectors for expression of heterologous genes in host cells are well known and can be used in the instant invention. For example, GST-Tat T23N vectors (encoding amino acid 1 through 72 and amino acid 1 through 48) have been produced for expression of Super-Tat in bacteria. RSV-Tat T23N (aa 1–72 and aa 1–48) vectors have also been produced for expression of Super-Tat in mammalian cells and for use in an in vitro coupled transcription and translation reaction. CMV-Tat-HA vectors have also been made for evaluation of expression of Tat in mammalian cells as well as for purification. Further, as will be understood by those of skill in the art upon reading this disclosure, various other vectors and host cells systems can also be used for recombinant expression of the Super-Tats of the present invention.

Thus, the present invention also relates to nucleic acid sequences encoding a Super-Tat of the present invention and vectors comprising such nucleic acid sequences. In addition, the present invention relates to host cells comprising these vectors which are capable of expressing Super-Tats of the present invention.

Super-Tats of the present invention are expected to be useful in inhibition of HIV replication. Tat function requires binding to TAR, an RNA element in the viral LTR that is synthesized in early in the transcription process. Thus, in one embodiment, Super-Tats of the present invention have been made that are defective in binding to TAR but still retain their ability to bind to P-TEFb. One variant, referred to herein as Super-TatK7, was produced by changing five arginines in the basic domain of Super Tat to lysines. Co-expression of this protein in cells along with wild-type Tat in LTR transactivation assays inhibited reporter gene expression 6.5 fold. Expression of this protein in cells infected with virus is expected to inhibit viral transcription by competing with viral Tat for binding to P-TEFb. It is believed that Super-Tat defective in TAR binding will be a more potent inhibitor of viral replication than wild-type Tat modified to be defective in binding to TAR as described by Modesti et al. (New Biol. 1991 3(8):759–68). Accordingly, the Super-Tats of the present invention can be used as an additional anti-viral compound to an existing anti-HIV drug regimen.

The Super-Tats of the present invention may also function as effective immunogens for raising anti-Tat antibodies. Antibodies against the Super-Tats of the present invention can be raised in accordance with well known techniques. These antibodies can then be incorporated into vaccines and administered to individuals to protect against HIV infection and to neutralize Tat mediated pathogenic effects in individuals already infected with HIV. Techniques for preparation of vaccines from antibodies are also well known.

In addition, the Super-Tats of the present invention may have a more accessible basic domain due to their unique conformation. Accordingly, the Super-Tats may activate the VEGF receptor more potently and may be useful as endothelial permeability factors.

As demonstrated herein, Super-Tats of the present invention interact more strongly with P-TEFb, particularly with its cyclin T1 subunit. Accordingly, the Super-Tats of the present invention can also be used in research applications in place of wild-type Tat. For example, to investigate the requirement for P-TEFb in transcription, nuclear extracts are depleted of endogenous P-TEFb by incubating them with a HIV Tat column. Purified P-TEFb can then be added back to the depleted extract in controlled amounts or at set intervals to investigate its role in transcriptional activity. A Super-Tat of the present invention can be used instead of wild-type Tat to more efficiently remove P-TEFb from these extracts. Further, lower amounts of the Super-Tat as compared to wild-type Tat can be used to achieve the same effect.

Use of anti-viral compounds to treat HIV fails to completely eradicate HIV infection (Siliciano, J. D. and Siliciano, R. F. J. Clin. Invest. 2000 106(7):823–5). This is believed to be due to the persistence of lymphocytes containing stably integrated, yet transcriptionally silent, proviruses. Occasional reactivation of these lymphocytes continues to provide a source of infection. It is believed that Super-Tat may selectively activate viral replication in resting cells and result in the enhanced clearance of these cells from the patients system. Alternatively Super-TatK7 may be utilized to further augment anti-retroviral therapy and enhance suppression of viral reactivation. Accordingly, treatment of patients with doses of Super-Tat or Super-TatK7, along with other anti-viral compounds is expected to be beneficial.

The present invention also relates to various compositions comprising a Super-Tat and their use in a variety of applications.

For example, chemically synthesized Super-Tats can be added to cell media for uptake by cells and subsequent viral activation. Chemically synthesized forms of this peptide are also useful for structural studies such as via 2-dimensional nuclear magnetic resonance (NMR) spectroscopy.

Tagged fusion constructs such as (multiple Histidine-tagged (HIS-tagged) or Hemagglutanin-tagged (HA-tagged) constructs, are useful primarily for production in cells followed by purification over an affinity column. The HA fusion construct of Super Tat is already known to be active in transactivation assays. Proteins expressed in cells often contain post-translational modifications including, but not limited to, acetylation, myristoylation and glycosylation, required for full in vivo function. The present invention also includes post-translational modified versions of Super-Tat.

Viral vectors containing Super-Tat are useful in studies of Tat transactivation and viral replication. Super-Tat can be incorporated into viral vectors including, but not limited to, adenovirus and retrovirus vectors in accordance with well known techniques.

Viral particles of HIV viruses and SHIV, a simian/human chimera virus, comprising Super-Tat of the present invention are useful for studying the effect of highly active Tat on viral replication and latency.

Stably transfected cell lines, such as mammalian cells stably transfected with Super-Tat, can be used for infection of various virus strains and to investigate the role of Super-Tat in the viral life cycle. Additionally, stably transfected cells can be used to propagate selected HIV viral strains that do not grow well under other conditions.

Conditioned medium from cells expressing Super-Tat can also be prepared. Animal cells expressing Tat normally release some amount of Tat into the medium. Thus, it is expected that cells expressing Super-Tat will also release some amount into the medium. This "conditioned" medium has many uses. For example, the conditioned medium can be used to purify Super-Tat. The conditioned medium can also be used as a growth medium for viral replication. HIV culture is often used as part of a panel of tests to confirm if an individual is infected. Use of the Super-Tat conditioned media is expected to enhance the sensitivity of these tests by decreasing the number of days required to detect viral replication.

Accordingly, the present invention also relates to the use of Super-Tat, and in particular, conditioned medium comprising Super-Tat in assays and kits for diagnosis of HIV infection in patients.

The following nonlimiting examples are provided to further illustrate the present invention.

EXAMPLES

Example 1

Production of a Super-Tat

The Tat gene from the HIV-NL4-3 molecular clone was subcloned into pUC19 vector (Yamisch et al. Gene 1985 33:103–119) after digestion with Bam HI and Sal I restriction enzymes. Mutagenic PCR, using the Quickchange Site-Directed Mutagenesis Kit (Stratagene, Calif.) was carried out using the primer pair CTG CTT GTA ACA ATT GCT AT (SEQ ID NO:1)/TTG TTA CAG CAG TTT TAG G (SEQ ID NO:2) to change the threonine at amino acid position 23 to asparagine. The sequence of the resulting Tat protein is MEPVDPRLEPWKHPGSQPKTACN(SEQ ID NO:3) \NCYCKKCCFHCQVCFITKALGI-SYGRKKRRQRRRAHQNSQTHQASLSKQ (SEQ ID NO:4). This construct is called pUC-Tat T23N.

Example 2

Measurement of Transcriptional Activity

A glutathione-S transferase tagged version of Tat T23N (1–72) was made by subcloning into the pGEX2T vector (Invitrogen). GST-Tat wild type (NL4-3) was also constructed. A Tat-associated kinase assay was carried out using U937 cell extract (Ramanathan et al. J. Virol. 1999 73(7): 5448–58). Briefly, U937 cells were treated with 5 ng/ml PMA (Sigma-Aldrich, MO) to induce P-TEFB. Cells were harvested and protein extracts prepared. The GST-Tat proteins were expressed in *E. coli* and bound to Glutathione-Sepharose beads (Amersham-Pharmacia, Sweden), washed several times and incubated with 400 micrograms of U937 cell extract to pull-down the endogenous P-TEFb complex. The beads were then washed again and a kinase reaction was performed with a synthetic CTD substrate and radiolabeled ATP. The reaction products were resolved on a SDS-polyacrylamide gel and the extent of CTD phosphorylation quantified on a Phosphoimager (Molecular Dynamics, Sweden). This experiment was also conducted using extracts of 293 cells. With either cell extract the P-TEFb complex bound to GST-Tat T23N phosphorylated CTD peptide 3.5-fold more than complex bound to wild-type Tat. The increased binding of GST-Tat T23N to endogenous P-TEFb was confirmed by immunoblotting to detect CDK9, the kinase subunit of P-TEFb.

Transcriptional transactivation of the HIV-1 LTR was measured by co-transfection experiments. The Tat gene from pUC-Tat T23N was subcloned into an RSV-driven expression vector pRc-RSV (Invitrogen, CA). U937 cells were electroporated with 4 μmicrograms of HIV-LTR-Luciferase, 7 micrograms of RSV-renilla Luciferase and 0.5 micrograms of RSV-Tat T23N or RSV-Tat wild-type (NL4-3). Cells ($1\times10^6$) were electroporated in 250 microliter of RPMI 1640 medium at 250 V, 1100 micro F and 186 Ohm resistance in 4 mm gap electroporation cuvettes. Cells were cultured in 10 ml growth medium (RPMI 1640+100% FBS) for 12 hours and harvested. Cell pellets were lysed in 50 microliter of Promega Lysis Buffer and 20 microliter was used in a Dual Luciferase Assay (Promega, WI). The transfection efficiency was normalized to renilla luciferase activity. In this assay Tat T23N transactivated 3-fold more than wild-type Tat.

What is claimed is:

1. An isolated variant protein of wild-type HIV-1 Tat protein comprising an asparagine at the amino acid residue corresponding to position 23 of SEQ ID NO: 3 and C-terminal amino acid sequence NCYCKKCCFHCQVCFITKALGISYGRKKRRQRRRAHQNSQTHQASLSKQ (SEQ ID NO:4), wherein said variant exhibits higher transcriptional activation and stronger P-TEFb binding than wild-type HIV-1 Tat.

2. An isolated nucleic acid sequence encoding the variant of claim 1.

3. A vector comprising the nucleic acid sequence of claim 2.

4. A host cell comprising the vector of claim 3.

5. A fusion protein comprising a selected protein fused to the variant of claim 1.

6. A tagged fusion construct comprising the variant of claim 1 fused to a tag for purification of the variant.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
ctgcttgtaa caattgctat                                                    20

<210> SEQ ID NO 2
<211> LENGTH: 19
```

-continued

```
<212> TYPE: DNA
<213> ORGANISM: Artificial sequence
<220> FEATURE:
<223> OTHER INFORMATION: Synthetic

<400> SEQUENCE: 2
ttgttacagc agttttagg                                                19

<210> SEQ ID NO 3
<211> LENGTH: 23
<212> TYPE: PRT
<213> ORGANISM: Artificial sequence
<220> FEATURE:
<223> OTHER INFORMATION: Synthetic

<400> SEQUENCE: 3

Met Glu Pro Val Asp Pro Arg Leu Glu Pro Trp Lys His Pro Gly Ser
1               5                   10                  15

Gln Pro Lys Thr Ala Cys Asn
            20

<210> SEQ ID NO 4
<211> LENGTH: 49
<212> TYPE: PRT
<213> ORGANISM: Artificial sequence
<220> FEATURE:
<223> OTHER INFORMATION: Synthetic

<400> SEQUENCE: 4

Asn Cys Tyr Cys Lys Lys Cys Cys Phe His Cys Gln Val Cys Phe Ile
1               5                   10                  15

Thr Lys Ala Leu Gly Ile Ser Tyr Gly Arg Lys Lys Arg Arg Gln Arg
            20                  25                  30

Arg Arg Ala His Gln Asn Ser Gln Thr His Gln Ala Ser Leu Ser Lys
        35                  40                  45

Gln
```